(12) United States Patent
Isaji et al.

(10) Patent No.: US 6,376,543 B1
(45) Date of Patent: Apr. 23, 2002

(54) SECONDARY CATARACT INHIBITOR

(75) Inventors: Masayuki Isaji; Hiroshi Miyata; Yukiyoshi Ajisawa, all of Nagano (JP)

(73) Assignee: Kissei Pharmaceuticals Co., Ltd. (JP)

( * ) Notice: Subject to any disclaimer, the term of this patent is extended or adjusted under 35 U.S.C. 154(b) by 0 days.

(21) Appl. No.: 09/269,200

(22) PCT Filed: Oct. 9, 1997

(86) PCT No.: PCT/JP97/03630

§ 371 Date: Mar. 31, 1999

§ 102(e) Date: Mar. 31, 1999

(87) PCT Pub. No.: WO98/16214

PCT Pub. Date: Apr. 23, 1998

(30) Foreign Application Priority Data

Oct. 14, 1996 (JP) ............................................. 8-306952

(51) Int. Cl.⁷ ............................................. A61K 31/195
(52) U.S. Cl. ....................................... 514/563; 514/912
(58) Field of Search ................................. 514/352, 535, 514/563, 912

(56) References Cited

PUBLICATIONS

Chemical Abstracts 126:288094 (1997)—Okamoto.*

* cited by examiner

*Primary Examiner*—Zohreh Fay
(74) *Attorney, Agent, or Firm*—Stuart D. Frenkel

(57) ABSTRACT

The present invention relates to a secondary cataract inhibitor comprising as the active ingredient N-(3,4-dimethoxycinnamoyl)anthranilic acid represented by the formula:

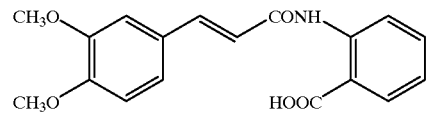

or a pharmaceutically acceptable salt thereof, which has an inhibitory activity on posterior capsule opacification formation after cataract surgery and is useful for the prevention or treatment of secondary cataract.

7 Claims, 1 Drawing Sheet

SECONDARY CATARACT INHIBITOR

FIELD OF THE INVENTION

The present invention relates to a pharmaceutical composition being useful as a secondary cataract inhibitor.

More particularly, the present invention relates to an inhibitor for secondary cataract after cataract surgery, which inhibitor comprises as the active ingredient N-(3,4-dimethoxycinnamoyl)-anthranilic acid represented by the formula:

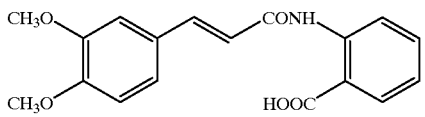

(I)

or a pharmaceutically acceptable salt thereof.

BACKGROUND OF THE INVENTION

Cataract is a refractory ocular disease which occurs and develops due to various factors. The discase subsequently leads to lower vision due to lens opacity. Most of this ocular discase is age-related senile cataract. The incidence of cataract is thought to be 60–70% in persons in their sixties and nearly 100% in persons eighty years old and more. In proceeding toward a society composed largely of elderly people, the prevention and treatment of cataract will become more important for the future. However, at the present time, there is no sure therapeutic agent which has an inhibitory activity on the development of cataract. Therefore, the development of an effective therapeutic agent has been desired. Presently, the treatment of cataract depends upon the correction of vision using eye glasses, contact lenses etc. or surgical operations such as insertion of an intraocular lens into the capsula lentis after extracapsular cataract extraction.

In cataract surgery, the incidence secondary cataract after surgery is been a problem. Secondary cataract is equated with opacity present on the surface of the remaining posterior capsule following extracapsular cataract extraction. The mechanism of secondary cataract is mainly as follows. After excising lens epithelial cells (anterior capsule), secondary cataract results from migration and proliferation of residual lens epithelial cells, which are not completely removed at the time of extraction of the lens cortex, onto the posterior capsule leading to posterior capsule opacification. Also, secondary cataract results from abnormal proliferation of the residual lens epithelial cells in the equator followed by formation of Elschnig pearls.

In cataract surgery, it is impossible to remove lens epithelial cells completely, and consequently it is difficult to always prevent secondary cataract. It is said that the incidence of the above posterior capsule opacification is 40–50% in aphakic eyes and 7–20% in pseudophakic eyes.

On the other hand, in the field of cataract medication, extensive study has been actively promoted in order to find substances capable of inhibiting secondary cataract. Up to now for example, it has been was confirmed that metabolic antagonists such as mitomycin, daunomysin, 5-FU and colchicine are effective secondary cataract inhibitors. However, concerns about these drugs have been raised in view of problems such as serious side effects which have been found [Atarashii Ganka, Vol. 12, No. 3, pp 451–452 (1995); Japanese Journal of Ophthalmic Surgery, Vol. 8, No. 3, pp. 439–446 (1995)] and accordingly, these drugs have not been used to use clinically. It has also been reported that the formation of secondary cataract was significantly inhibited when an inserted intraocular lens was coated with indometacin. Further ethylenediaminetetraacetic acid (EDTA) has been found effective in inhibiting secondary cataract [Japanese Journal of Ophthalmic Surgery, Vol. 8, No. 3, pp. 439–446 (1995); IOL & RS, Vol. 19, No. 2, pp. 78–82 (1995); Japanese Patent Application Publication (kokai) No.Hei. 8-175984]. However, clinically satisfactory drugs for preventing and inhibiting secondary cataract have not been developed.

N-(3,4-dimethoxycinnamoyl)anthranilic acid (generic name: Tranilast) represented by the above formula (I) of the present invention has been widely used in medicines for the treatment of allergic disorders such as bronchial asthma, allergic rhinitis, atopic dermatitis and allergic conjunctivitis, as well as cutaneous disorders such as keloid and hypertrophic scar. For example, it has been known that Tranilast has inhibitory activities on chemical mediator release caused by an allergic reaction, excessive collagen accumulation by fibroblast cells in cutaneous tissues and excessive proliferation of smooth muscle cells in coronary artery vessels.

However, it has not been previously disclosed that Tranilast has an inhibitory activity on secondary cataract formation and it until now has not been known that Tranilast is can be useful as an inhibitor for secondary cataract.

SUMMARY OF THE INVENTION

The present invention relates to a secondary cataract inhibitor which comprises as the active ingredient N-(3,4-dimethoxycinnamoyl)anthranilic acid represented by the formula:

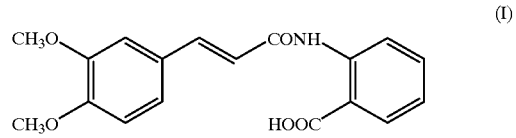

(I)

or a pharmaceutically acceptable salt thereof.

The present invention also relates to a method for the prevention or treatment of secondary cataract which comprises administering N-(3,4-dimethoxycinnamoyl) anthranilic acid represented by the above formula (I) or a pharmaceutically acceptable salt thereof.

The present invention also relates to use of N-(3,4-dimethoxycinnamoyl)anthranilic acid represented by the above formula (I) or a pharmaceutically acceptable salt thereof for the manufacture of a pharmaceutical composition for the prevention or treatment of secondary cataract.

Furthermore, the present invention relates to use of N-(3, 4-dimethoxycinnamoyl)anthranilic acid represented by the above formula (I) or a pharmaceutically acceptable salt thereof as a secondary cataract inhibitor.

DETAILED DESCRIPTION OF THE INVENTION

Figure 1:
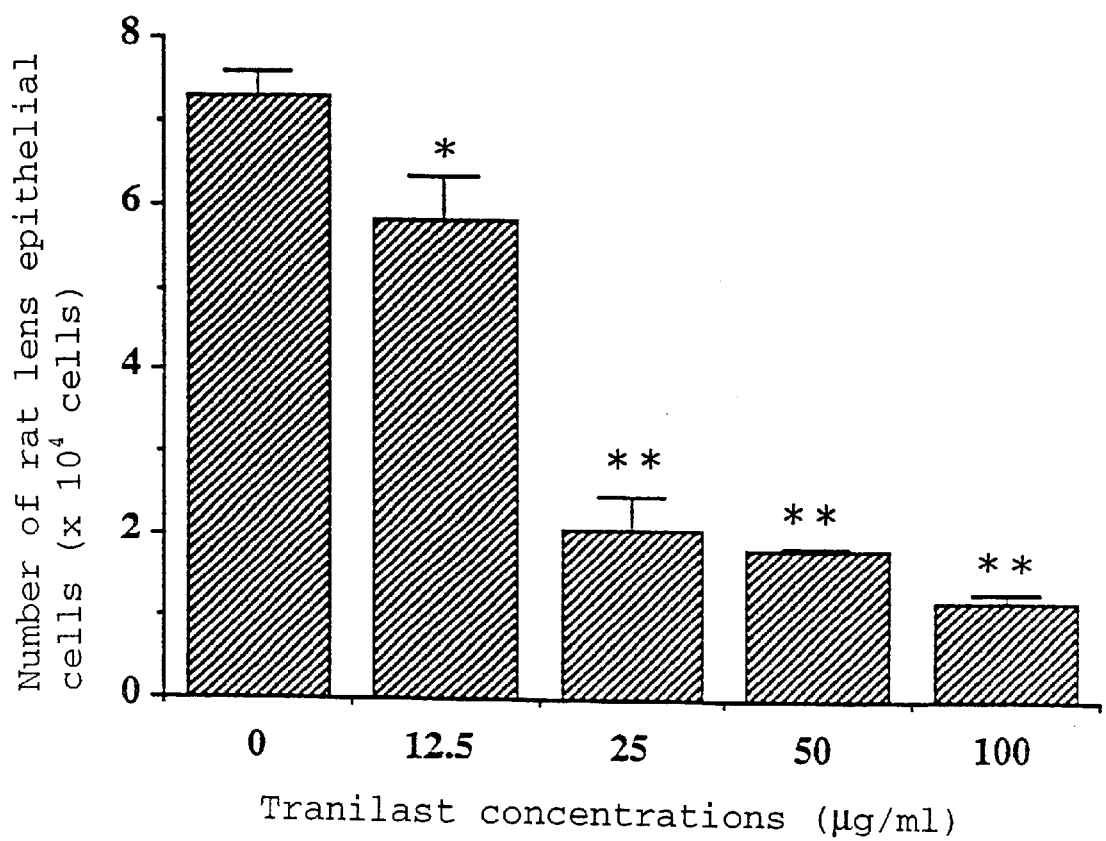
FIG. 1 is a graph illustrating an inhibitory activity on rat lens epithelial cell proliferation by Tranilast. The axis of the ordinates shows number of rat lens epithelial cells (x10$^4$ cells), and the axis of the abscissas shows Tranilast concentrations to be added ($\mu$g/ml). The symbols * and ** in the graph show the significantly difference at p<0.05 and p<0.01, respectively.

The present inventors have extensively studied in order to find compounds having an inhibitory activity on secondary cataract formation. As a result, it was found that N-(3,4-dimethoxy-cinnamoyl) anthranilic acid represented by the above formula (I) of the present invention has a marked inhibitory effect on lens epithelial cell proliferation and is extremely useful as a secondary cataract inhibitor, thereby forming the basis of the present invention.

The present inventors have shown that Tranilast significantly suppress proliferation of lens epithelial cells in in vitro testing using rat lens epithelial cells.

Accordingly, it is believed that Tranilast has an excellent inhibitory effect on lens epithelial cell proliferation and consequently is an extremely useful compound as a secondary cataract inhibitor.

Therefore, pharmaceutical compositions which are useful as secondary cataract inhibitors comprise as the active ingredient Tranilast or a pharmaceutically acceptable salt thereof.

Various methods for the preparation of Tranilast and salts thereof which are active ingredients are known and these compounds can be readily prepared according to methods described in literature and the like (Japanese Patent Application Publication (kokoku) No.Sho.56-40710; ibid. No.Sho.57-36905; ibid. No.Sho 58-17186; ibid. No.Sho.58-48545; ibid. No.Sho.58-55138; ibid. No.Sho.58-55139; ibid. No.Hei.01-28013; ibid. No.Hei.01-50219; ibid. No.Hei.03-37539 etc.).

As examples of pharmaceutically acceptable salts of Tranilast, salts with inorganic bases such as a sodium salt and a potassium salt, salts formed with organic amines such as morpholine, piperazine and pyrrolidine and salts formed with amino acids can be illustrated.

When the pharmaceutical compositions of the present invention are employed as a practical treatment, various dosage forms of the pharmaceutical compositions can be used depending. Preferably, eyedrops, injections, eye ointments or methods such as in plantation after incorporating composition into pellet or microcapsule form and insertion after pre-coating the intraocular lens can be illustrated.

These pharmaceutical compositions can be formulated by admixing, diluting or dissolving Tranilast, optionally, with appropriate pharmaceutical additives such as excipients, disintegrators, binders, lubricants, diluents, buffers, isotonicities, antiseptics, moistening agents, emulsifiers, dispersing agents, stabilizing agents and dissolving aids in accordance with conventional methods and formulating in a conventional manner depending upon the dosage form.

For example, eyedrops can be formulated by dissolving Tranilast or a pharmaceutically acceptable salt together with a basic substance with heating in sterilized water in which a surface active agent is dissolved, adding polyvinylpirrolidone, optionally adding appropriate pharmaceutical additives such as a preservative, a stabilizing agent, a buffer, an isotonicity, an antioxidant and a viscosity improver, and dissolving completely.

Injections can be directly injected into diseased tissues such as cornea, crystalline lens and vitreous or their adjacent tissues by using a fine needle, and can be also used as intraocular perfusate.

The pharmaceutical compositions of the present invention can be administered as sustained release preparations. For example, Tranilast or a salt thereof can be incorporated into a pellet or microcapsule of a sustained release polymer as a carrier, and the pellet or microcapsule surgically in planted into the tissues to be treated. Also, Tranilast or a salt thereof can be applied by inserting an intraocular lens pre-planted with the Tranilast composition. As examples of sustained release polymers, ethylene-vinylacatate copolymer, polyhydromethacrylate, polyacrylamide, polyvinylpirrolidone, methylcellulose, lactic acid polymer, lactic acid-glycolic acid copolymer and the like can be illustrated. Preferably, a biodegradable polymer such as lactic acid polymer and lactic acid-glycolic acid copolymer can be illustrated.

When the pharmaceutical compositions of the present invention are employed as a practical treatment, the dosage of Tranilast or a pharmaceutically acceptable salt thereof as the active ingredient is appropriately decided depending on the body weight, age, sex, degree of symptoms of each patient to be treated. For example, when instilling to eyes, these compounds can be administered approximately within the range of from 10 $\mu$g to 50 mg per day per adult human.

The dose of Tranilast or a pharmaceutically acceptable salt thereof can be appropriately increased or decreased depending on the degree of symptoms present and therapeutic value of such dosage on each patient to be treated.

The present invention is further illustrated in more detail by way of the following Examples.

EXAMPLE

Inhibitory Activity on Lens Epithelial Cell Proliferation

① Culture of Rat Lens Epithelial Cells

Rat crystalline lens was harvested and cut into narrow strips. The strips were adhered to a culture plate and subcultured in Dulbecco's modified Eagle's Medium (DMEM) containing 10% fetal calf serum (FBS) at 37° C. in an atmosphere of 5% $CO_2$ in air for 4 days. On day 4 (at the point that lens epithelial cells had migrated and profilated from crystalline lens tissues), the medium was aspirated and cells were gently washed with phosphate-buffered saline (PBS(-)). Then, the PBS(-) was aspirated, an aliquot of 0.25% trypsin solution containing 0.02% EDTA was added to the culture plate, and the morphology of the cells was observed under phase-contrast microscopy. When cells were going to be round, an equal value of DMEM containing 10% FBS was added to the trypsin solution to stop the action of trypsin. Attached cells were harvested from the plate by pipetting the medium using a slender pasture pipette. The cell suspension was transferred into spit, then medium was added to the spit, and the cell suspension was mixed about 20 times vigorously by pipetting with a pasture pipette and centrifuged at 100–110×g for 1 minute. After the supernatant was discarded, fresh medium was added to the precipitate, and the lens epithelial cell suspension was prepared by pipetting using a pasture pipette. The suspension was further subcultured in DMEM containing 10% FBS to use for experiments.

② Preparation of Test Drugs

Tranilast was added to a 1% aqueous sodium bicarbonate solution to prepare a 1.0% solution and dissolved by warming at 70° C. The solution was sterilized with a millipore filter and diluted with DMEM containing 10% FBS to a final prescribed concentration.

③ Experimental Method

Cell suspension ($2 \times 10^4$ cells/0.1 ml) and DMEM medium (1.9 ml) containing various concentration of Tranilast and 10% FBS were added to a culture plate (60 mm), and cultured at 37° C. in an atmosphere of 5% $CO_2$ in air. After 4 days, the medium was aspirated, the cells were washed with PBS(-), and 1 ml of 0.25 % trypsin solution containing 0.02% EDTA was added to the plate. After harvesting cells from the plate by pipetting using a pasture pipette, the number of viable cells was counted using a hemocytometer.

④ Assessment of Effect

Mean and standard variation values of each group were calculated. Statistical analysis of significance was performed by a one-way analysis of variance and statistical significance was confirmed. Thereafter, analysis of significance between groups was performed by Dunnett's multiple test.

⑤ Results

As shown in FIG. 1, Tranilast significantly suppressed the proliferation of lens epithelial cells in a concentration-dependent manner.

Industrial Applicability

A pharmaceutical composition comprising as the active ingredient Tranilast or a pharmaceutically acceptable salt thereof has marked inhibitory activity on lens epithelial cell proliferation and is suitable as a secondary cataract inhibitor.

What is claimed is:

1. A method for the prevention or treatment of secondary cataract which comprises administering subsequent to cataract surgery N-(3,4-dimethoxycinnamoyl)anthranilic acid represented by the formula:

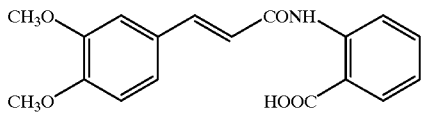

or a pharmaceutically acceptable salt thereof.

2. The method of claim 1, wherein said N-(3,4 dimethoxycinnamoyl)anthranilic acid or pharmaceutically acceptable salt thereof is administered in the form of eye-drops.

3. The method of claim 1, wherein said N-(3,4 dimethoxycinnamoyl)anthranilic acid or pharmaceutically acceptable salt thereof is administered in the form of an eye ointment.

4. The method of claim 1, wherein said N-(3,4 dimethoxycinnamoyl)anthranilic acid or pharmaceutically acceptable salt thereof is implanted into ocular tissue.

5. The method of claim 4, wherein said N-(3,4 dimethoxycinnamoyl)anthranilic acid or pharmaceutically acceptable salt thereof is formed into a pellet or microcapsule comprising a sustained release polymer as a carrier for said N-(3,4 dimethoxycinnamoyl)anthranilic acid.

6. The method of claim 5, wherein said sustained release polymer is a lactic acid polymer or a lactic acid-glycolic acid copolymer.

7. The method of claim 2, wherein said N-(3,4 dimethoxycinnamoyl)anthranilic acid or pharmaceutically acceptable salt thereof is administered subsequent to extracapsular cataract extraction.

* * * * *